United States Patent [19]
Yamamoto et al.

[11] 4,204,917
[45] May 27, 1980

[54] METHOD FOR MEASURING ION ACTIVITY

[75] Inventors: Tadao Yamamoto, Machida; Hiroshi Takekawa, Kunitachi; Taichi Banno, Hachioji; Kiyozo Koshiishi, Sagamihara, all of Japan

[73] Assignee: Olympus Optical Company Limited, Tokyo, Japan

[21] Appl. No.: 970,239

[22] Filed: Dec. 18, 1978

Related U.S. Application Data
[62] Division of Ser. No. 739,052, Nov. 5, 1976.

[30] Foreign Application Priority Data
Nov. 10, 1975 [JP] Japan .................. 50-134836

[51] Int. Cl.² ............................................. G01N 27/46
[52] U.S. Cl. ............................. 204/1 T; 422/63; 422/64; 422/72; 422/98
[58] Field of Search ............... 204/1 T, 195 R, 195 M, 204/195 G; 422/50, 63, 64, 72, 98

[56] References Cited

U.S. PATENT DOCUMENTS

| | | | |
|---|---|---|---|
| 2,566,676 | 9/1951 | Rabbitts | 204/195 R |
| 3,267,362 | 8/1966 | Page | 204/195 R |
| 3,498,889 | 3/1970 | Imredy et al. | 204/195 P |
| 3,499,733 | 3/1970 | Abbott et al. | 422/64 |
| 3,615,236 | 10/1971 | Tamm | 422/64 |
| 3,625,850 | 12/1971 | Arrington | 204/195 R |
| 3,744,974 | 7/1973 | Maddox et al. | 422/72 |
| 3,867,273 | 2/1975 | Gilbert | 204/1 T |
| 4,007,011 | 2/1977 | Greaves et al. | 422/50 |
| 4,048,040 | 9/1977 | Schwartz | 204/195 R |
| 4,054,416 | 10/1977 | Duff | 422/64 |

Primary Examiner—T. Tung
Attorney, Agent, or Firm—Toren, McGeady and Stanger

[57] ABSTRACT

In the disclosed method, ion activity is measured by placing a cup filled with a test solution to be measured on a cup receiver, lifting a cup lifting arm to engage the cup receiver with a rotary plate, rotating the rotary plate to stir the test solution in the cup, measuring a potential difference between a reference electrode and other electrodes after completion of the stirring of the solution, and indicating the ion activity as a function of the potential differences.

11 Claims, 6 Drawing Figures

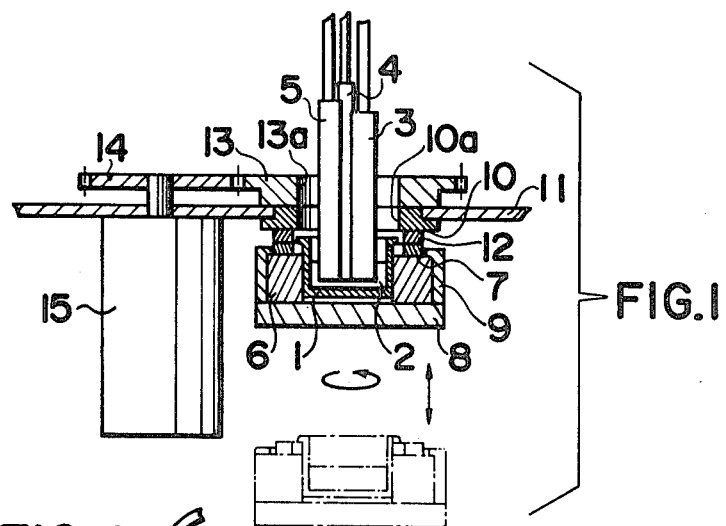
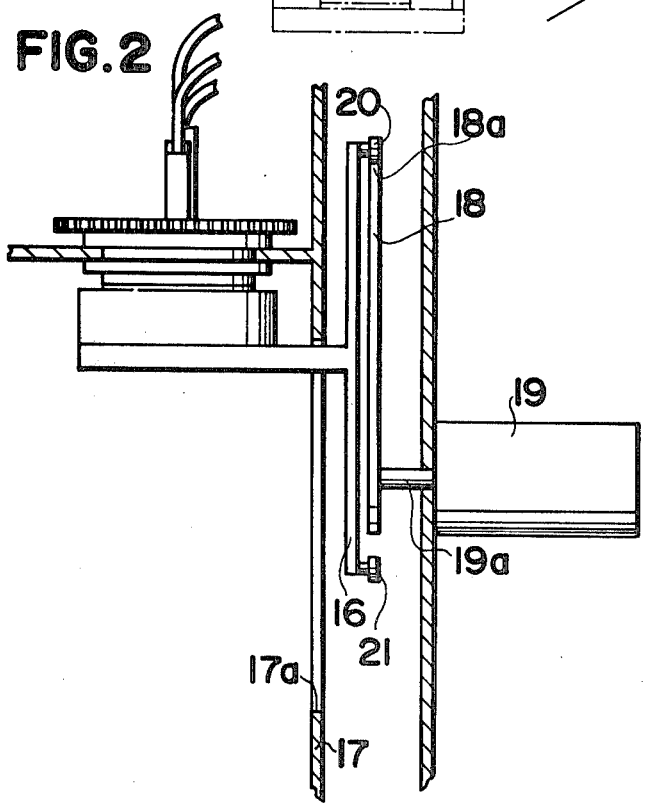

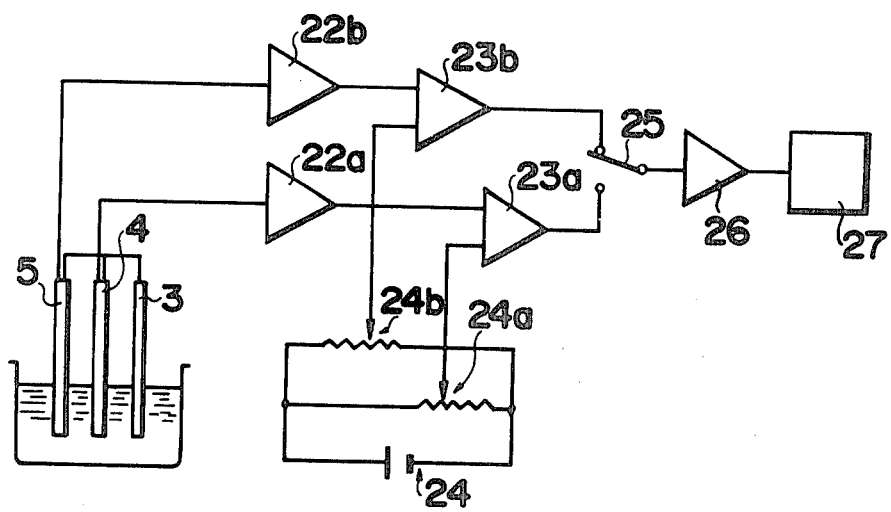
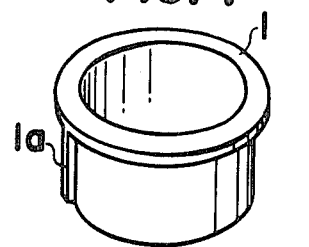
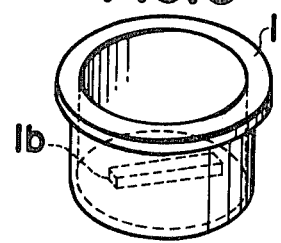
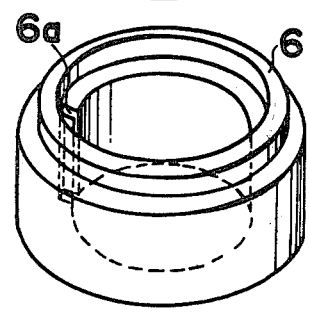
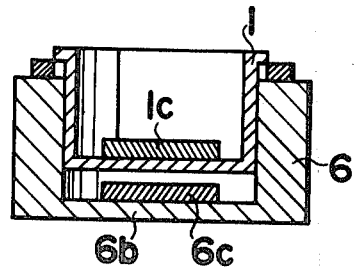

METHOD FOR MEASURING ION ACTIVITY

This is a division of application Ser. No. 739,052, filed Nov. 5, 1976.

BACKGROUND OF THE INVENTION

1. Field of the Invention

The present invention relates to a method for measuring the activity of chemically special ions in humor or body fluid.

2. Description of the Prior Art

It is known that, among others, sodium (Na) and potassium (K) ions in body fluids play a physiologically important role. That is, Na and K ions occupy about 90% of a cation in serum and they are the most important components for osmotic pressure and acid radical and base equilibrium of the serum. Further, measurement of ions in the serum for representing cellular body fluid is important because conditions such as the water content, electrolytic metabolism and excitability of nerves, muscles, etc. can be diagnosed. Further, increase and decrease of the ion concentration plays a major role for diagnosing clinical diseases, such as diarrhea, hyperhydration, functional disorder of the heart, emesis and the like.

From the reasons explained in the foregoing measurement of various kinds of ions in a body fluid is carried out, but the most important is the measurement of Na ions and K ions. The latter may be measured a flame method or an atomic absorbing method. These methods, however, have many problems involving preparation before measurement, operationability and setting conditions. Moreoover, these measuring methods derive the ion quantity in a sample instead of the activity of ions in a sample. Hence these methods are insufficient for the above-described purpose.

SUMMARY OF THE INVENTION

An object of the present invention is to eliminate the above described defects of the conventional method.

Another object of the present invention is to provide an apparatus for measuring ion activity, particularly for measuring chemically special ion activity, i.e., Na and K ion activities, in body fluid promptly and directly.

The present invention involves a method of measuring ion activity in which electrodes are used for generating a potential in selective response to the ion to be measured and this potential is measured by a measuring circuit and displayed as a digital value.

According to the present invention, an apparatus for measuring ion activity comprises a reference electrode, at least one electrode for selectively responding to at least one ion to be measured, a rotary plate surrounding and rotating around said electrode, a cup receiver for placing a cup filled with a test solution to be measured, a cup-lifting arm constructed to rotatably hold and vertically move said cup receiver, and a measuring circuit including an amplifier for measuring a potential difference between said reference electrode and each of the above other electrodes and a reverse logarithm amplifier or the like.

BRIEF DESCRIPTION OF THE DRAWING

FIG. 1 is a cross-sectional view of an apparatus for measuring ion activity according to the present invention;

FIG. 2 is a cross-sectional view showing the lifting mechanism thereof;

FIG. 3 is a circuit diagram showing an outline of the measuring circuit of the apparatus and FIGS. 4–6 are a perspective view and a cross-sectional view showing another embodiments of a cup for filling a test solution therein.

DESCRIPTION OF THE PREFERRED EMBODIMENT

Referring now to FIG. 1 one embodiment of an apparatus for measuring ion activity according to the present invention is shown.

A cup made of plastic or the like receives a test solution 2. An electrode 3 serves as a reference electrode, an electrode 4 for sodium, and an electrode 5 for potassium. All are fixed at a predetermined position and height by a suitable means, and at the position shown in FIG. 1. The electrode 5 is inserted into the test solution 2 in cup 1. Reference numeral 6 represents a cylindrical cup receiver, 7 a ring-shaped friction plate made of sponge and the like and fixed on the upper surface of cup receiver 6. A cup lifting arm 8 is vertically moved by a means explained later, and an outer frame 9 is mounted on the cup lifting arm 8 and held for rotating the cup receiver 6 in the outer frame. A rotary plate 10 with an opening 10a is rotatably secured to a securing plate 11 and permits insertion of the electrodes at the center thereof. On the lower surface of the rotary plate 10 is fixed a ring-shaped friction plate 12 made of the same material and having the same diameter as that of friction plate 7. On the upper surface of rotary plate 10 is secured a gear 13 which has a central opening 13a for permitting entry of the electrodes. Reference numeral 14 represents another gear clutched with the gear 13 and rotated by a motor 15 fixed to the securing plate 11. Therefore, when the cup 1 is at the lifted position shown by a solid line in FIG. 1, and if the motor 15 is rotated, the rotary plate 10 is rotated by the gear 14 and the gear 13, and the fixed ring-shaped friction plate 12 integrally secured thereto is also rotated. The friction plate 12 comes into contact with the friction plate 7 fixed at the upper surface of the cup receiver, so that the frictionally transmitted cup receiver 6 and subsequently the cup 1 rotate within the outer frame 9.

The lifting mechanism of the cup lifting arm is explained below. As shown in FIG. 2 (viewed from the side of FIG. 1), reference numeral 16 represents vertically moving plate to which the cup lifting arm 8 is fixed. A guide plate 17 contains an elongated hole 17a which guides lifting arm 8 when it is vertically moved. Reference numeral 18 represents an eccentric cam rotated by a motor 19. The surface of the eccentric cam 18 comes into contact with a roller 20 secured to the vertically movable plate 16. Therefore, the eccentric cam 18 is rotated by rotation of the motor 19, and the roller 20 contacting with the cam 18 is vertically moved by rotation of the cam 18. As a result, the vertically movable plate 16 is also shifted and vertically moved along the elongated hole 17a of the guide plate 17. The cup 1 placed on lifting arm 8 is vertically moved together with vertical movement of the lifting arm 18. Thus, when the eccentric cam 18 is positioned as shown in FIG. 2, the cup lifting arm 8 is positioned such that both the friction plates 7 and 12 are adjacent to each other at the highest position, as shown in FIG. 1. When the eccentric cam 18 is rotated by the motor 19, the cup lifting arm 8 is lowered. Thus, the latter may be lowered to the position shown by dotted lines in FIG. 1. Further, a roller 21 provided at the other end (lower end portion) of the vertically movable plate 16 is provided for coercively lowering the lifting arm 8 when it cannot be lowered by dead weight in case that a face 18a farthest from an axis 19a is moved downwards. That is, when the cam surface of the eccentric cam 18 is moved by its rotation, if the roller 20 is not lowered along the cam surface, the roller 20 is lowered by pushing the other roller 21 with the cam surface, and the vertically movable plate 16 and the lifting arm 8 are coercively pushed down, so that the lifting arm 8 is positively lowered to the position shown by a dotted line in FIG. 1 in any case.

FIG. 3 shows a measuring circuit used in the apparatus according to the invention. In FIG. 3, reference numeals 3, 4 and 5 represents the aforementioned electrodes. Amplifiers 22a and 22b are respectively connected to the electrode 4 for sodium and the electrode 5 for potassium. The outputs of these amplifiers are connected to input terminals of differential amplifiers 23a and 23b, respectively. Reference numeral 24 represents a circuit for calibration. A circuit for sodium 24a is connected to one input terminal of the differential 23a, while a circuit 24b for potassium is connected to an input terminal of the differential amplifier 23b. Furthermore, the outputs of these differential amplifiers are connected to a reverse logarithm amplifier 26 through a switch 25 and digitally indicated by means of a digital meter 27. The potential difference between the reference electrode 3 and the electrode 4 for sodium ions is amplified by the amplifier 22a. A difference from the circuit for calibration is taken as the output, and the reverse logarithm of the output from the differential amplifier 23a is digitally indicated by the reverse logarithm amplifier 26. Therefore the ion activity can directly be obtained as a digital amount in units of milliequivalent/liter.

The function of the apparatus having the above explained construction according to the invention is explained below. At first, a test solution in which ion activity is known is put in the cup. The lifting arm 8 is at the position shown by a dotted line in FIG. 1, and the cup lifted with the test solution is placed within the cup receiver 6. The eccentric cam 18 is rotated by the motor 19, and lifting arm 8 is raised together with the vertically movable plate 16. When the lifting arm 8 is raised as high as possible, rotation of the motor 19 is stopped and the motor 15 is rotated. As a result, the rotary plate 10 is rotated.

When the lifting arm 8 is elevated, as shown by a solid line in FIG. 1 and the friction plate 12 fixed to the rotary plate 10 comes into contact with the friction plate 7 fixed to the upper surface of the cup receiver 6, the rotation of the rotary plate 10 is transmitted to the cup receiver 6 through both the friction plates 12 and 7. Consequently, the cup receiver 6 is rotated. Thus, rotation of the cup receiver 6 in the outer frame 9 makes the cup 1 rotate and the known test solution 2 is stirred. When the test solution 2 is thoroughly stirred, rotation of the motor 15 stops. Rotation of the cup is stopped to allow it to stand still for a certain time, and thereafter measurement is carried out. At first, switch 25 is set at the terminal of the amplifier for sodium, and the measured value is read out by the digital meter as described above. In order to make the value indicated in the digital meter at that instant equal to the known value, the resistance value of the circuit for calibration is changed and corrected. Then switch 25 is switched to the potassium side and the measured value is read in the same manner.

Similarly, correction is carried out by operating a calibration dial. After calibration is thus completed, motor 19 is rotated and the eccentric cam 18 is rotated, thereby lowering the cup lifting arm 8 to the position of the dotted lines as described above and taking the cup out of the cup receiver 6.

An unknown sample to be inspected is diluted with a buffer solution of predetermined magnification, is put into the cup 1. The cup 1 is placed on the cup receiver 6 as described above and a start button (not shown) is pressed. Then, the operation as explained afore is repeated, and the measured values of the sample to be inspected, i.e., the activity of sodium ions and the activity of potassium ion, are respectively indicated in the digital meter.

In such an apparatus, when rotating the cup receiver 6 for the purpose of stirring the test solution, slippage may occur between the cup 1 and the cup receiver 6 and prevent thorough rotation. In order to prevent such slippage, a key 1a projects from the outside of the cup 1 and a key groove 6a is formed in the cup receiver 6 as shown in FIG. 4. Further, in the cup shown in FIG. 1, the test solution in the cup can be stirred by such rotation, and particularly, because the electrode is arranged in the test solution, the stirring action is increased. However, if a plate-shaped stirrer 1b as shown in FIG. 5, is fixed at the inner bottom surface of the cup 1, the stirring effect can be increased. Further, the embodiment shown in FIG. 6 indicates that a bottom surface 6b is provided in the cup receiver 6 and a magnet 6c is fixed thereto, while in the inner bottom surface of the cup 1 is fixed a magnet 1c. Therefore it becomes possible to obtain efficient rotation and stirring without any slip by integrally rotating the cup 1 and the cup receiver 6 due to the attractive force of these magnets. Further, the magnet 1c provided in the cup 1 plays a role as a stirrer, so that a stirring effect is increased.

As explained previously, according to the apparatus for measuring ion activity of the present invention, a test body is merely placed on the cup receiver in the apparatus and an operation button is pushed. Then the aforementioned operation, i.e., the stirring of the test solution, measurement of a potential difference between the electrodes etc., can be performed automatically, and the measured value is indicated digitally, so that there is nothing to do but read the value. As compared with the known flame method and atomic absorption method, the present invention is much simpler in preparation and operation, and the measured value to be sought is not an ion amount but an ion activity in the sample. The present invention is particularly useful for measurement of sodium ions and potassium ions in body fluids. Further, for the method involving a common ion electrode, a potential difference between the electrodes is measured and the ion activity is obtained by conversion. However, in an advantage of the apparatus according to the present invention, resides in the fact that the ion activity itself can be read out as a digital value.

What is claimed is:

1. A method of measuring ion activity comprising placing a cup filled with test solution to be measured on a cup receiver, lifting a cup lifting arm to engage said cup receiver with a rotary plate, rotating the cup by rotating said rotary plate to stir the test solution in the cup, measuring a potential difference between a reference electrode and another electrode after completion of the stirring of the solution, and indicating the ion activity to be measured.

2. The method as in claim 1, wherein the ion activity to be measured is indicated digitally.

3. The method as in claim 2 wherein potential differences are measured between the reference electrode and a plurality of other electrodes after completion of the stirring of the solution.

4. The method as in claim 2, wherein the plate is made to engage the top of the cup receiver and the plate has an opening.

5. The method as in claim 4, further comprising causing the electrodes to project through the opening in the plate.

6. The method as in claim 1, wherein potential differences are measured between the reference electrode and a plurality of other electrodes after completion of the stirring of the solution.

7. The method as in claim 1, wherein the relative positions of the electrodes and the rotatable plate are kept fixed and a vertical mover lifts the cup receiver up and down relative to the plate.

8. The method as in claim 1, wherein the cup receiver and the plate are caused to engage each other frictionally.

9. The method as in claim 1, further comprising projecting the electrodes through a central opening in the plate.

10. The method as in claim 1, further comprising driving the cup with the cup receiver by interlocking one to the other with a key and groove.

11. The method as in claim 1, further comprising maintaining the relative positions of the cup and the cup receiver magnetically.

* * * * *